US00PP33699P2

(12) United States Plant Patent
Bacon et al.

(10) Patent No.: US PP33,699 P2
(45) Date of Patent: Nov. 30, 2021

(54) NECTARINE TREE NAMED 'SUNECT28'

(50) Latin Name: ***Prunus persica* var. *nucipersica***
Varietal Denomination: SUNECT28

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/202,936

(22) Filed: Mar. 16, 2021

(51) Int. Cl.
*A01H 5/08* (2018.01)

(52) U.S. Cl.
USPC ..... Plt./190

(58) Field of Classification Search
USPC ..... Plt./187, 190, 191
See application file for complete search history.

*Primary Examiner* — Susan McCormick Ewoldt
(74) *Attorney, Agent, or Firm* — Knobbe, Martens, Olson & Bear, LLP

(57) ABSTRACT

A new and distinct variety of nectarine tree, *Prunus persica* var. *nucipersica*, cv. 'Sunect28', is characterized by early to midseason ripening, circular, sweet, very large-sized fruit having very firm flesh and a medium brix value.

1 Drawing Sheet

Latin name of the genus and species claimed: *Prunus persica* var. *nucipersica*.

Variety denomination: 'SUNECT28'.

BACKGROUND AND SUMMARY OF THE INVENTION

This invention relates to the discovery and asexual propagation of a new and distinct variety of nectarine, *Prunus persica* var. *nucipersica* cv. 'Sunect28'. The new variety was first originated by hybridization and identified in June 2015 by Terry A. Bacon and Terrence J. Frett as breeder number 'NE1741'. The new variety was first evaluated by Terry A. Bacon and Terrence J. Frett near Wasco, Calif. in Kern County.

The new variety 'Sunect28' is characterized by early to midseason ripening, circular, very large-sized, sweet fruit with very firm flesh and a medium brix value.

The pollen parent is 'NE999Z' (unpatented breeding selection), and the seed parent is 'NE1048' (unpatented breeding selection). The parent varieties were first crossed in February 2012, the date of first sowing being February 2013 and the date of first flowering being February 2015. The new nectarine variety 'Sunect28' was first asexually propagated by Terry A. Bacon and Terrence J. Frett near Wasco, Kern County, Calif. in February 2016 by dormant grafting.

The new variety 'Sunect28' is distinguished from its seed parent, 'NE1048' in that the fruit of the new variety ripens about 24 days later than the fruit of the seed parent. The new variety 'Sunect28' also has a larger fruit weight of 190 g compared to a fruit weight of 140 g for 'NE1048'. The new variety 'Sunect28' also has a higher brix:acid ratio at 19 compared to 12 for 'NE1048'.

The new variety 'Sunect28' is distinguished from its pollen parent, 'NE999Z' in that the fruit of the new variety ripens about 15 days later than that of the pollen parent. The new variety 'Sunect28' also has a larger fruit weight of 190 g compared to 146 g for 'NE999Z'. The new variety 'Sunect28' also has a higher brix:acid ratio at 19 compared to 14 for 'NE999Z'.

The new variety 'Sunect28' resembles 'Honey May' (U.S. Plant Pat. No. 19,363) in that the fruit of both varieties has yellow flesh and ripens at about the same time. The new variety 'Sunect28' differs from 'Honey May' in that the fruit of the new variety has a brix of 14% and a Brix:Acid ratio of 20, compared to a brix of 12% and a Brix:Acid ratio of 9 for 'Honey May'. The new variety 'Sunect28' also differs from 'Honey May' in that the fruit weight of the new variety is 190 g compared to 145 g for 'Honey May'.

The new variety 'Sunect28' resembles 'Spring Bright' (U.S. Plant Pat. No. 7,507) in that the fruit of both varieties has yellow flesh. The new variety 'Sunect28' differs from 'Spring Bright' in that the fruit weight of the new variety is 190 g compared to 155 g for 'Spring Bright'. The new variety 'Sunect28' differs from 'Spring Bright' in that the ripening of the fruit of the new variety starts about 12 days earlier than 'Spring Bright'.

The new variety 'Sunect28' differs from 'Sunectwentyone' (U.S. Plant Pat. No. 18,114) in that the ripening of the fruit of the new variety starts about 19 days later than that of 'Sunectwentyone'. In addition the fruit of the new variety has a a Brix:Acid ratio of 19, compared to a Brix:Acid ratio of 13 for the fruit of 'Sunectwentyone'.

The new variety 'Sunect28' has been shown to maintain its distinguishing characteristics through successive asexual propagations by, for example, cuttings and grafting.

BRIEF DESCRIPTION OF THE PHOTOGRAPH

The accompanying color photographic illustration shows typical specimens of the foliage and fruit of the new nectarine variety 'Sunect28'. The illustration shows the upper and lower surface of the leaves, an exterior and sectional view of a fruit divided across its suture plane to show flesh color, pit cavity and the stone. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 3-year-old 'Sunect28' plants grown in Wasco, Kern County, Calif., and is believed to apply to plants of the variety grown under similar conditions of soil and climate elsewhere. Observations were made in 2019.

TREE

General: (Measurements were taken on 3-year-old trees unless otherwise noted.).

*Size*.—Large. Normal for most nectarine varieties.

*Spread*.—Normal for most nectarine varieties. Reaches a spread of 5 m with normal vase pruning.

*Vigor*.—Strong. Approximately 1.8 to 2 meters of growth in the first growing season.

*Growth*.—Semi-upright.

*Productivity*.—Very productive, about 126 lb/tree and about 900 25 lb cartons per acre.

*Bearer*.—On one-year old shoots.

*Fertility*.—Self-compatible.

*Hardiness*.—Hardy in all fruit growing areas of California.

*Disease resistance/susceptibility*.—No specific testing for relative plant disease resistance/susceptibility has been undertaken. Under close observation in Kern County, Calif., no particular plant/fruit disease resistance/susceptibility has been observed.

*Chilling requirements*.—About 250 hours at or below 7.2° C.

*Shipping and storage characteristics*.—Fruit stores well for six weeks at 0° C.

*Market use*.—Table grape.

Trunk: (Measurements were taken at approximately 30 cm above the soil line.).

*Diameter*.—Approximately 15 cm.

*Texture*.—Medium shaggy, increasing with age.

*Trunk color*.—About medium Greyed-Orange 173A becoming darker with age.

Branches: (Measurements were taken at approximately 90 cm above the soil line.).

*Size*.—Approximately 10 cm.

*Texture*.—Smooth on young wood, increasing roughness with tree age.

*Color*.—About medium Greyed-Orange 173A becoming darker with age.

*Lenticels*.—Present.

*Lenticels numbers*.—Plentiful.

*Lenticels density*.—Approximately 12 per $cm^2$.

*Lenticels color*.—About Light Grey 201D.

*Lenticels length*.—Approximately 3 mm.

*Lenticels width*.—Approximately 1 mm.

One year old shoots: (Data taken in September at the midpoint of current-season growth.).

*Size*.—Average diameter approximately 5 mm.

*Color*.—Topside: About Medium Greyed-Orange 164B. Underside: About Medium Greyed-Orange 164B.

*Internode length*.—About 2.0 cm, midway on shoot.

*Lenticels diameter*.—About 0.3 mm.

*Lenticels*.—Plentiful.

*Lenticels color*.—About White 155D.

*Intensity of anthocyanin on upper side of shoots*.—Absent or very sparse.

Vegetative buds: (Data were taken in September at the midpoint of current-season growth.).

*Position of vegetative bud in relation to shoot*.—Slightly held out.

*Size*.—Medium, approximately 1.5 mm×2.5 mm.

*Shape*.—Ovoid.

*Shape of apex*.—Obtuse.

*Color*.—About Dark Brown 200B.

Flower buds: (Data were taken in September at the midpoint of current-season growth.).

*Distribution*.—2 flowers buds per node, on one-year old shoots.

*Shape*.—Rounded.

*Dimensions*.—Approximately 4 mm×2.5 mm.

*Color*.—About Dark Greyed-Orange 165A.

*Ratio of flower buds to vegetative buds*.—2 flowers buds: 1 vegetative bud.

FOLIAGE

Leaves: (Data taken on fully expanded leaves).

*Size*.—Medium.

*Average length*.—Long; approximately 12.0 cm without petiole.

*Average width*.—Medium; approximately 3.0 cm.

*Ratio of length to width*.—Very elongated, approximately 4:1 ratio.

*Shape*.—Lanceolate.

*Color of upper side*.—About Dark Green 139A.

*Color of lower side*.—About Medium Green 139B.

*Glossiness of upper side*.—Medium.

*Angle at apex* (*excluding tip*).—Acute.

*Shape of base*.—Cuneate.

*Venation*.—Pinately net veined.

*Vein color*.—About Light Green 139D.

*Surface texture*.—Smooth.

*Shape in cross-section*.—Concave.

*Profile*.—Up-folded.

*Leaf blade tip*.—Curved downward.

*Undulation of margin*.—Slight.

*Density of pubescence of lower side*.—Absent or very sparse.

*Incisions of margin*.—Crenate.

Petiole:

*Length*.—Medium; approximately 10 mm.

*Diameter*.—Approximately 0.7 mm.

*Color*.—About Light Green 138C.

Stipules:

*Number/leaf bud*.—Approximately 2 when present.

*Typical length*.—Medium, approximately 8 mm.

*Color*.—About Dark Greyed-Red 180A when dried.

*Persistence*.—Falls off.

Leaf glands:
*Form*.—Reniform.
*Average number and arrangement*.—0-4, usually 3, arranged alternately.
*Diameter*.—Approximately 1 mm.
*Color*.—About Dark Greyed-Red 180A when dry.
*Position of nectaries* (*glands*).—Mainly on the petiole, sometimes on base of leaf.

FLOWERS

General:
*Time of beginning of flowering*.—Very early for the San Joaquin Valley, Calif.
*Flower blooming period*.—First bloom: Approximately February 8 in Wasco, Calif. Location of First bloom: Toward base of the tree. Full bloom: Approximately February 12 in Wasco, Calif. Location of Full bloom: Central part of the tree canopy.
*Duration of bloom*.—Approximately 10 days.
*Flower diameter*.—Medium, approximately 34 mm.
*Flower form*.—Showy.
Pedicel:
*Length*.—Long, approximately 10 mm.
*Diameter*.—Approximately 1 mm.
*Color*.—About Dark Greyed-Red 180A when dry.
*Pubescence*.—Absent.
Sepals:
*Number*.—5.
*Length*.—Approximately 6 mm.
*Diameter*.—Approximately 4 mm.
*Shape*.—Triangular.
*Color*.—About Medium Red 44A.
*Texture*.—Smooth to slightly bumpy.
*Margins*.—Smooth.
*Position*.—Adpressed to petals.
*Frequency of flowers with double sepals*.—None.
Receptical:
*Depth*.—Medium, approximately 2 mm.
*Pubescence of inner surface*.—Absent.
*Pubescence of outer surface*.—Absent.
Petals:
*Number*.—5.
*Arrangement*.—Slightly overlapping.
*Color*.—About Medium Red-Purple 62C.
*Surface texture*.—Smooth.
*Length*.—Long, approximately 18 mm.
*Width*.—Approximately 15 mm.
*Shape*.—Circular.
*Apex shape*.—Rounded.
*Base shape*.—Narrows at point of attachment.
*Undulation of margin*.—Medium.
*Frequency of flowers with double petals*.—Never.
Pistil:
*Length*.—Approximately 37 mm.
*Ovary diameter*.—Approximately 1.5 mm.
*Pubescence*.—Absent.
*Stigma extension in comparison to anthers*.—Above.
*Frequency of supplementary pistils*.—Few.
Stamens:
*Number*.—Approximately 32-38. Average 34.
*Length*.—Variable, ranging approximately from 3 mm to 10 mm.
*Filament color*.—About White 155A.
*Pollen color*.—About Medium Red 52A.
*Position*.—Perigynous.

FRUIT

General: (Description taken near Wasco, Kern County, Calif.).
*Time of beginning of fruit ripening*.—Early to midseason for the San Joaquin Valley, Calif.
*Harvest*.—
*Date of first pick*.—Approximately May 28.
*Date of last pick*.—Approximately June 7.
Maturity when described: Firm-mature.
Peduncle:
*Length of stem*.—Short, approximately 7 mm.
*Diameter of stem*.—Approximately 7 mm.
*Color of stem*.—About Medium Greyed-Orange 164B.
Size:
*Average size*.—Very large.
*Diameter in line with suture plane*.—Approximately 69 mm.
*Diameter perpendicular to suture*.—Broad, approximately 69 mm.
*Average weight*.—Approximately 190 gm.
*Height*.—Tall, approximately 69 mm.
Shape:
*Viewed from apex*.—Circular.
*In lateral view, perpendicular to suture*.—Circular.
*In-line with suture*.—Circular.
*Symmetry*.—Symmetric or slightly asymmetric.
*Shape of base*.—Slightly depressed.
*Shape of apex*.—Rounded.
*Depth of stalk cavity*.—Medium, approximately 10 mm.
*Width of stalk cavity*.—Medium, approximately 20 mm.
*Depth of suture*.—Absent or very shallow.
Skin:
*Thickness*.—Medium, typical of most varieties.
*Adherence to flesh*.—Strong.
*Surface texture*.—Nearly smooth.
*Taste*.—Neutral.
*Reticulation*.—Absent.
*Tendency to crack*.—Rare.
*Pubescence*.—Absent.
*Bloom on skin*.—Absent or very week.
*Ground color*.—About Medium Yellow 13C.
*Relative area of over color of skin*.—Nearly whole surface.
*Overcolor*.—About Dark Red, ranging from Dark Red 53C to Dark Red 53A.
*Pattern of over color of skin*.—Solid.
*Number of lenticels*.—None to a few.
*Size of lenticels*.—Very small approximately 0.5 mm.
Flesh:
*Ripens*.—Evenly.
*Texture*.—Slow-softening, melting, firm-juicy.
*Color*.—About Medium Yellow 13C.
*Flavor*.—Sweet.
*Firmness*.—Very firm.
*Juiciness*.—Medium, able to squeeze free juice easily.
*Acidity*.—Medium for nectarines, 0.75% titratable acidity.
*Sweetness*.—Medium.

*Brix*.—Approximately 14% at harvest.
*Adherence of stone to flesh*.—Adherent.
*Fiber*.—Medium.

Stone:

*Stone freeness*.—Clings.
*Stone size*.—Size: Medium. Length: Approximately 12 mm. Diameter in line with suture: Approximately 10 mm. Diameter perpendicular to suture: Approximately 10 mm.
*Color*.—About Light Greyed-Orange 164C.
*Position of maximum diameter*.—Middle.
*Stone shape*.—Lateral view: Medium elliptic. Basal view: Broad elliptic. Ventral view: Broad elliptic.
*Base shape*.—Nearly straight.
*Apex shape*.—Pointed.
*Ridges*.—Rounded throughout.
*Outgrowing keel*.—Well developed.
*Ventrical edge*.—Medium.
*Dorsal edge*.—Full, deep grooves.
*Fibers*.—Retains short fiber-like threads along ridges.
*Symmetry in lateral view*.—Symmetric.
*Texture of lateral surface*.—Rough.
*Width of stalk-end*.—Medium, approximately 4 mm.
*Tendency to split*.—Rare.

What is claimed is:

1. A new and distinct nectarine tree as herein described and illustrated.

* * * * *

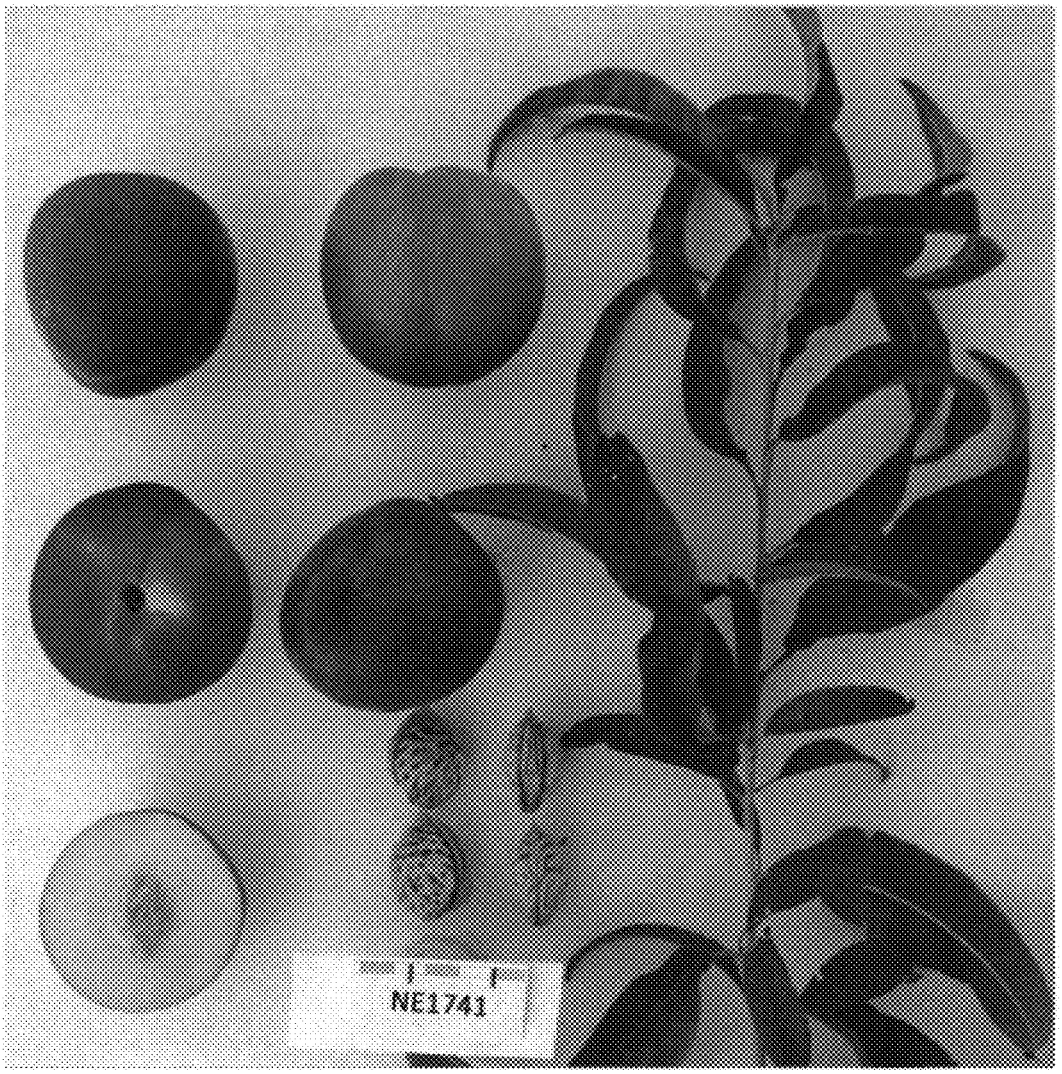
NE1741